US012629090B2

(12) United States Patent
Jo

(10) Patent No.: US 12,629,090 B2
(45) Date of Patent: May 19, 2026

(54) DEVICE FOR MEASURING ERECTILE FUNCTION AND ERECTILE FUNCTION TEST SYSTEM

(71) Applicant: Jung Ki Jo, Seoul (KR)

(72) Inventor: Jung Ki Jo, Seoul (KR)

( * ) Notice: Subject to any disclaimer, the term of this patent is extended or adjusted under 35 U.S.C. 154(b) by 890 days.

(21) Appl. No.: 17/321,785

(22) Filed: May 17, 2021

(65) Prior Publication Data

US 2021/0267536 A1     Sep. 2, 2021

Related U.S. Application Data

(63) Continuation of application No. PCT/KR2019/015982, filed on Nov. 20, 2019.

(30) Foreign Application Priority Data

Nov. 20, 2018     (KR) ........................ 10-2018-0143935
Nov. 20, 2019     (KR) ........................ 10-2019-0149741

(51) Int. Cl.
*A61B 5/00*          (2006.01)
*A61B 5/107*        (2006.01)
(Continued)

(52) U.S. Cl.
CPC .......... *A61B 5/4393* (2013.01); *A61B 5/0022* (2013.01); *A61B 5/1075* (2013.01);
(Continued)

(58) Field of Classification Search
CPC ... A61B 5/4393; A61B 5/0022; A61B 5/0077; A61B 5/1075; A61B 2562/0247;
(Continued)

(56) References Cited

U.S. PATENT DOCUMENTS 6,050,959 A * 4/2000 Card .................... A61B 5/4368
600/587
2003/0139896 A1* 7/2003 Dietz .................... A61B 5/103
702/153

(Continued)

FOREIGN PATENT DOCUMENTS

KR         20160104428 A  * 9/2016
KR   1020160104428 A     9/2016
(Continued)

OTHER PUBLICATIONS

International Search Report of PCT/KR2019/015982 dated Mar. 2, 2020.

*Primary Examiner* — Jason M Sims
*Assistant Examiner* — Kyle W. Kretzer
(74) *Attorney, Agent, or Firm* — Dinsmore & Shobl LLP; Yongsok Choi, Esq.

(57) ABSTRACT

A device for measuring penile erectile function and an erectile function test system are provided. The device for measuring penile erectile function may include a body unit having a mesh structure formed of stretchable material and configured to surround at least a portion of a penis, a sensor unit arranged on the mesh structure of the body unit and configured to measure first data representing position information on penis, a storage unit configured to store the first data, and a communication unit configured to communicate the first data with a computing device.

6 Claims, 12 Drawing Sheets

(51) Int. Cl.
   *G01B 7/28* (2006.01)
   *G01B 11/24* (2006.01)

(52) U.S. Cl.
   CPC .............. *A61B 5/6813* (2013.01); *G01B 7/28* (2013.01); *G01B 11/24* (2013.01); *A61B 2562/0247* (2013.01)

(58) Field of Classification Search
   CPC .......... A61B 5/6823; A61B 2562/0219; A61B 2562/0261; A61B 5/1071; A61B 5/107; A61B 5/1073; A61B 5/6813; G16H 10/60; G16H 30/20; G16H 30/40; G16H 50/30; G16H 50/50
   See application file for complete search history.

(56) References Cited

U.S. PATENT DOCUMENTS

| | | | | |
|---|---|---|---|---|
| 2014/0171767 | A1* | 6/2014 | Hotaling | A61B 5/4393<br>600/323 |
| 2021/0251562 | A1* | 8/2021 | Jain | G16H 50/20 |

FOREIGN PATENT DOCUMENTS

| | | | |
|---|---|---|---|
| KR | 1020170035722 | A | 3/2017 |
| KR | 101916104 | B1 | 11/2018 |
| WO | 2018101786 | A1 | 6/2018 |

* cited by examiner

DEVICE FOR MEASURING ERECTILE FUNCTION AND ERECTILE FUNCTION TEST SYSTEM

CROSS-REFERENCE TO RELATED APPLICATIONS

The present application is a continuation of International Patent Application No. PCT/KR2019/015982, filed Nov. 20, 2019, which is based upon and claims the benefit of priorities to Korean Patent Application No. 10-2018-0143935, filed on Nov. 20, 2018 and Korean Patent Application No. 10-2019-0149741, filed on Nov. 20, 2019. The disclosures of the above-listed applications are hereby incorporated by reference herein in their entirety.

TECHNICAL FIELD

The present disclosure relates to a device for measuring penile erectile function and an erectile function test system, and relates to a device for measuring penile erectile function and an erectile function test system, which are worn by a test subject who is a male during nighttime sleep or during the day, thus measuring a change in a penis during an erection, and capable of testing the erectile ability of the male based on the change in the penis.

BACKGROUND ART

Erectile dysfunction refers to the inability to attain or maintain erection sufficient for satisfactory sexual performance. The erectile dysfunction may be caused by psychological factors such as stress, and may also be caused by physical factors such as smoking, diabetes, aging, and the like. The former is called psychogenic erectile dysfunction, and the latter is called organic erectile dysfunction. For example, as research shows, since the penile erection during sleep occurs without consciousness, the psychogenic erectile dysfunction is normal reaction, but the organic erectile dysfunction is abnormal reaction.

Erectile test (e.g., sleep erection test) is used as one of the diagnosing methods of such erectile dysfunction. However, this related erection test has the following problems.

First, there is a problem that a wearer can experience discomfort while a test object for the related erection test is worn on his penis. For example, the related erection test adopts a configuration having an elastic band to be brought into contact with the penis to measure the degree of changes in the elastic band's resistance as the elastic band is stretched and contracted according to the expansion and contraction of the penis to thus measure the change in length of the circumference of the penis. However, since the size of the penis varies from person to person, and also differs before and after erection, the portion for measuring the circumference of the penis need to be variable in a fairly large range, but the related art is limited because only the elasticity of the rubber band is used. As an example, when measuring the length of the circumference of the penis after an erection of a person with a large penis, the tension of the rubber band is strong, which may cause discomfort to the person wearing it. Furthermore, in the case of sleep erection test, there is a possibility that such discomfort can make proper test itself impossible due to disturbed sleep.

There is another related erection test having a measuring unit that is entirely a sensor surrounding the penis, and it has disadvantages that cost is excessive, and even when a portion of the sensor fails, this could lead into the entire device not functioning. Moreover, there is a limitation in the method of showing erection information to the user by simply providing the values of length and stiffness.

SUMMARY

Technical Problem

The present disclosure relates to a device for measuring penile erectile function and an erectile function test system, and has an object to improve wearing comfort when worn during night sleep or during the day for measuring and examining shape change of the penis during an erection, to provide economic feasibility and durability, and to provide detailed information on erectile ability (erectile function).

Technical Solution

A device for measuring penile erectile function according to an embodiment of the present disclosure may include: a body unit having a mesh structure formed of stretchable material and configured to surround at least a portion of a penis; a sensor unit arranged on the mesh structure of the body unit and configured to measure first data representing position information on penis; a storage unit configured to store the first data; and a communication unit configured to communicate the first data with a computing device.

A device for measuring penile erectile function according to another embodiment of the present disclosure may include: a body unit having a mesh structure formed of stretchable material and configured to surround at least a portion of a penis; a sensor unit arranged on the mesh structure of the body unit and configured to measure first data representing position information on the penis; a control unit configured to generate information on shape change of the penis based on the first data; a storage unit configured to store at least one of the first data and the information on shape change of the penis; a communication unit configured to communicate at least one of the first data and the information on shape change of the penis with a computing device, in which the sensor unit may be configured to include at least two sensor groups, and the information on shape change of the penis may be configured to include 3D image information.

In the device for measuring penile erectile function according to another embodiment of the present disclosure, a portion of the body unit may have a mesh structure formed of stretchable material, and the remaining portion of the body unit may be formed of non-stretchable material.

The erectile function test system of the penile erectile function according to an embodiment of the present disclosure may include at least one device for measuring penile erectile function; and a computing device, in which each of the one or more devices for measuring penile erectile function may include: a body unit having a mesh structure formed of stretchable material and configured to surround at least a portion of a penis; a sensor unit arranged on the mesh structure of the body unit and configured to measure first data representing position information on the penis; a storage unit configured to store the first data; and a communication unit configured to communicate the first data with a computing device, and the computing device may include: a control unit configured to generate information on shape change of the penis based on the first data; a storage unit configured to store at least one of the first data and the information on shape change of the penis; a communication unit configured to communicate at least one of the first data and the information on shape change of the penis with at least one of the one or more devices for measuring penile erectile function and an external computing device; and an output unit configured to output the information on shape change of the penis.

Advantageous Effects

According to various embodiments of the present disclosure, a body unit having a mesh structure formed of stretchable material has the effect of having both the stretchability of the material and the structural stretchability, thereby improving wearing comfort, and also reducing the disturbance of sleep of a subject for measurement, which results in more accurate measurement and examination of erectile function.

According to various embodiments of the present disclosure, it is possible to measure and test the erectile function by arranging an appropriate number of sensors on a portion of the body unit without requiring the entire body unit be formed of sensor, and accordingly, it is economical and also has excellent durability because it is possible to measure and test erectile function with the other sensors even when a portion of the sensors fails.

According to various embodiments of the present disclosure, the erectile function test system may provide information on shape change of the penis including 3D image information, thus providing a visually excellent effect by allowing the user to see a variety of information such as length, circumference, and degree of curvature at a glance.

BRIEF DESCRIPTION OF DRAWINGS

Embodiments of the present disclosure will be described with reference to the accompanying drawings described below, where similar reference numerals indicate similar elements, but embodiments are not limited thereto.

DETAILED DESCRIPTION OF THE INVENTION

Figure 1:
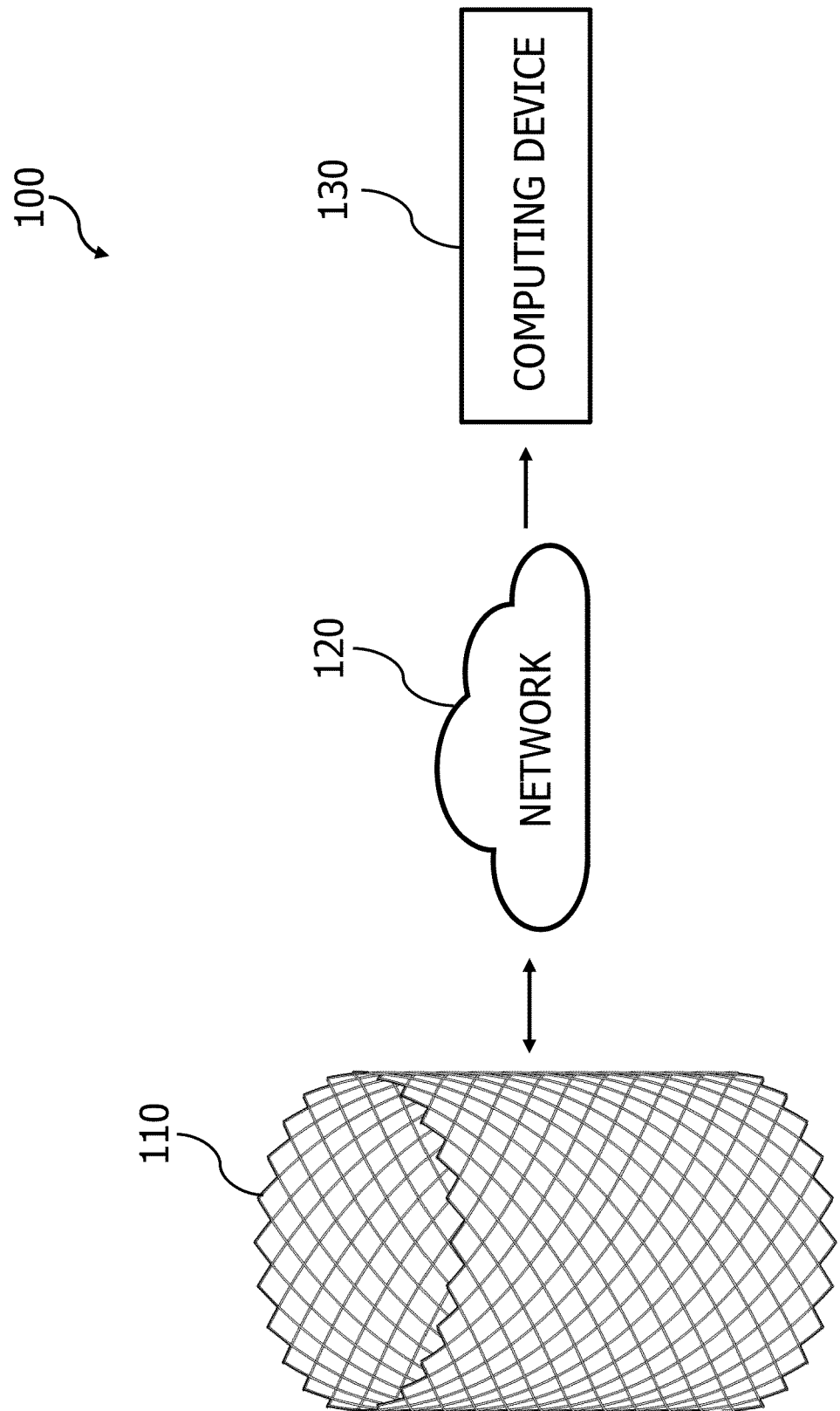
FIG. 1 is a schematic diagram of an erectile function test system according to an embodiment of the present disclosure.

Hereinafter, specific details for the practice of the present disclosure will be described in detail with reference to the accompanying drawings. However, in the following description, detailed descriptions of well-known functions or configurations will be omitted when it may make the subject matter of the present disclosure rather unclear.

In the accompanying drawings, the same or corresponding elements are assigned the same reference numerals. In addition, in the following description of the embodiments, duplicate descriptions of the same or corresponding elements may be omitted. However, even if descriptions of elements are omitted, it is not intended that such elements are not included in any embodiment.

FIG. 1 is a schematic diagram of an erectile function test system 100 according to an embodiment of the present disclosure. The erectile function test system 100 may be configured to include a device 110 for measuring penile erectile function, a network 120, and a computing device 130.

The device 110 for measuring penile erectile function may be configured to be worn on a subject for measurement (e.g., a patient with erectile dysfunction) to measure the erectile function. The device 110 for measuring penile erectile function may be configured to surround at least a portion of the penis, measure data representing penis information, store the measured data, and communicate, through a network, measurement data representing penis information or information on shape change of the penis generated based on the data, with the computing device through the network 120. According to an embodiment, the device 110 for measuring penile erectile function may have a mesh structure formed of stretchable material and configured to surround at least a portion of the penis such that it may be configured to measure and store first data representing position information on the penis through a sensor provided in the device 110 for measuring penile erectile function and communicate the stored first data to the computing device 130.

In FIG. 1, it is illustrated that the erectile function test system 100 includes one device 110 for measuring penile erectile function, but it may be configured such that one or more devices for measuring penile erectile function may be included in the erectile function test system 100. As an example, a plurality of devices for measuring penile erectile function may be configured to communicate with the computing device 130 to communicate the information on the penis measured from each of the plurality of devices for measuring penile erectile function with the computing device 130.

The network 120 may include a local area network and/or a long distance network. According to an embodiment, the network 120 may be configured with a wireless Internet method such as Bluetooth, Wi-Fi, WiBro, ultra-wideband, and the like. Alternatively, the network 120 may include a wired Internet method such as IEEE 1394, Ethernet, and the like.

According to an embodiment, the computing device 130 may be configured to receive measurement data representing the penis information from the device 110 for measuring penile erectile function through the network 120, and generate information on shape change of the penis based on the received data and output the information. For example, the computing device 130 may be a server device or a smartphone device.

Figure 2:
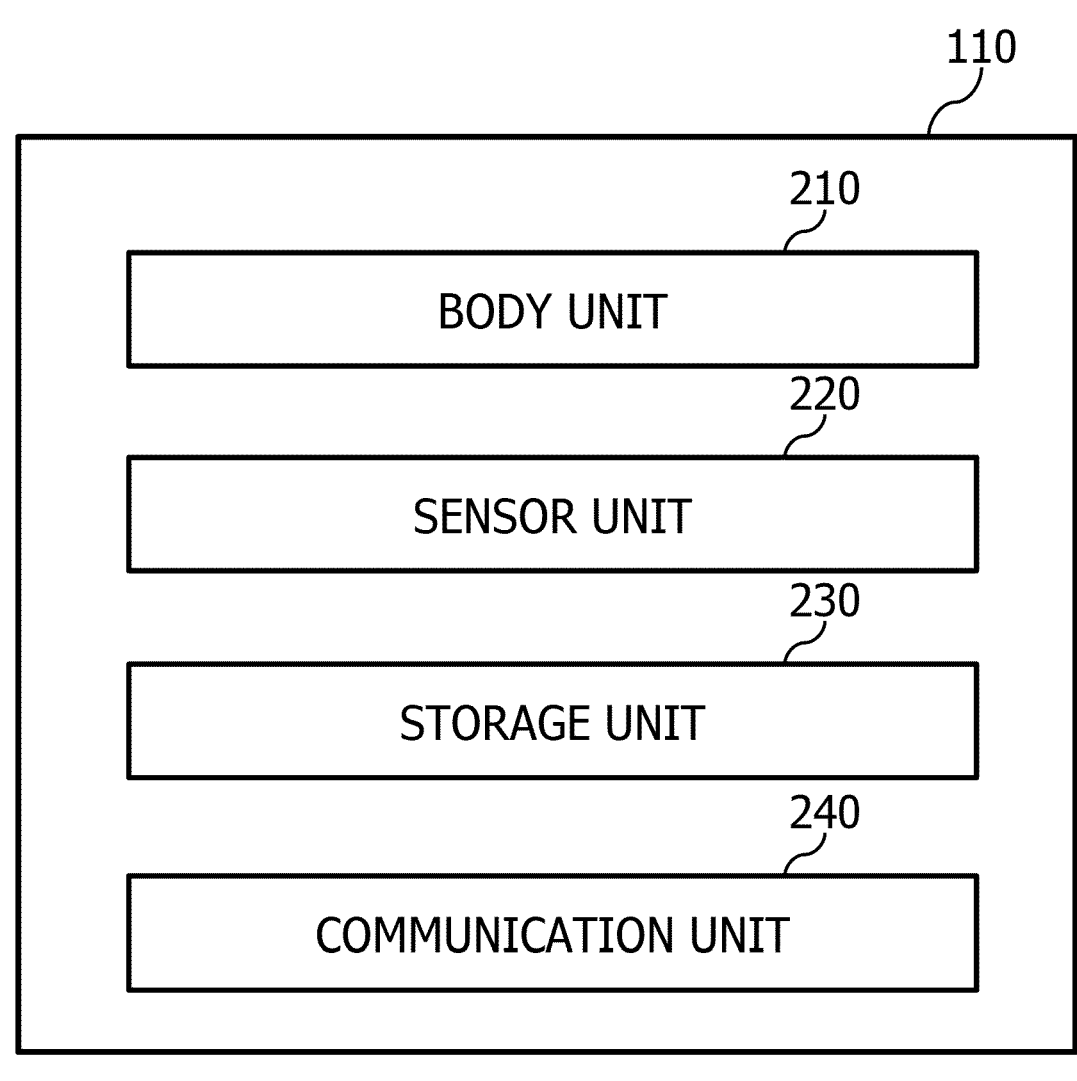
FIG. 2 is a block diagram illustrating in detail a configuration of the device for measuring penile erectile function according to an embodiment of the present disclosure.

FIG. 2 is a block diagram illustrating in detail the configuration of the device 110 for measuring penile erectile function according to an embodiment of the present disclosure. The device 110 for measuring penile erectile function may be configured to include a body unit 210, a sensor unit 220, a storage unit 230, and a communication unit 240. According to an embodiment, the device 110 for measuring penile erectile function may include the body unit 210 having a mesh structure formed of stretchable material and configured to surround at least a portion of the penis, the sensor unit 220 arranged on the mesh structure of the body unit and configured to measure the first data representing position information on the penis, the storage unit 230 configured to store the first data, and the communication unit 240 configured to communicate the first data with the computing device 130.

The body unit 210 may have a mesh structure formed of stretchable material, and may be configured to surround at least a portion of the penis. According to an embodiment, the body unit 210 may be configured to be stretchable in a longitudinal direction and/or a circumferential direction according to a shape change of the penis before and after erection. For example, the stretchable material may be a material including rubber, but is not limited thereto.

According to an embodiment, the mesh structure of the body unit 210 may be configured such that the nodes of the mesh structure form a figure that is in rhombus shape. Furthermore, the rhombus shape of the mesh structure of the body unit 210 may be configured to be deformable from a horizontally elongated shape to a vertically elongated shape, or from the vertically elongated shape to the horizontally elongated shape according to a shape change of the penis. This variability of the mesh structure can provide structural stretchability to the body unit.

The body unit 210 having the mesh structure formed of stretchable material has an effect of having both the stretchability of the material and the structural stretchability. For example, the body unit 210 having a mesh structure formed of stretchable material may be configured such that a material including rubber may be stretched and contracted, and the mesh structure may be stretched and contracted while the rhombus shapes formed by the nodes are transformed from the horizontally elongated shape to the vertically elongated shape, or vice versa. Due to such stretchability, the body unit 210 having the mesh structure formed of stretchable material may improve the wearing comfort of the subject for measurement because the tension is not high even when the penis is large or after the erection. Furthermore, since the body unit 210 having the mesh structure formed of stretchable material can reduce disturbance of the sleep of the subject for measurement, it facilitates accurate measurement and examination of erectile function.

The sensor unit 220 may be configured of at least one sensor. The sensor unit 220 may be configured of the same type of sensors or may be configured of various types of sensors in combination. According to an embodiment, the sensor may include a position sensor and/or a pressure sensor and/or a temperature sensor. According to still another embodiment, the sensor unit 220 may include at least one of an inertia measurement unit (IMU) including an acceleration sensor and a gyro sensor, an optical marker, and a stretchable sensor (e.g., e-textile, stretch sensor).

According to an embodiment, the sensor unit 220 may be configured to measure the first data representing position information on the penis. According to another embodiment, the sensor unit 220 may be configured to measure the first data representing position information on the penis and/or second data representing pressure information of the penis. According to still another embodiment, the sensor unit 220 may measure arbitrary data and/or information, which is used for generating the first data representing position information on the penis and/or the second data representing pressure information of the penis.

According to an embodiment, the sensor unit 220 may be arranged on the mesh structure of the body unit 210. For example, the sensor of the sensor unit 220 may be arranged on at least one of the nodes of the mesh structure. According to an embodiment, two position sensors may be arranged to be spaced apart from each other in the circumferential direction of the mesh structure in order to generate circumference information of a penis, and the sensor may be configured to measure absolute or relative position information on the penis. According to the present embodiment, it is economical, since it is possible to measure and test the erectile function by arranging an appropriate number of sensors without requiring the entire body unit 210 be formed of sensor. In addition, according to the present embodiment, even when some of the sensors, for example, any one of the three sensors arranged in the circumferential direction fails, it is possible to measure and test the erectile function with the rest of the sensors, and accordingly, excellent durability can be provided. In the related art in which the elastic band serves as both a sensor and a body that surrounds the penis, there is a disadvantage in that the entire elastic band needs to be formed of a sensor, and that the entire device cannot function even when only a part of the circuit in the elastic band is open. According to this embodiment, compared to the related art, there is an effect of higher economic feasibility and durability.

The storage unit 230 may be configured to store data representing penis information measured at the sensor unit. According to an embodiment, the storage unit 230 may be configured to store the first data representing position information on the penis. For example, the storage unit 230 may be one of an embedded multi-media card (eMMC), a micro SD card, and the like, but is not limited thereto.

According to an embodiment, the storage unit 230 may be attached onto the mesh structure of the body unit. According to another embodiment, it may be configured in a structure formed separately from the mesh structure of the body unit. For example, it may be attached adjacent to an end of the mesh structure of the body unit in the longitudinal direction so as not to interfere with the stretchability of the remaining portion, or may be configured in a separately formed structure on one side of the circumference of the mesh structure.

The communication unit 240 may be configured to communicate the data representing penis information with the computing device 130. According to an embodiment, the communication unit 240 may be configured to communicate the first data representing position information on the penis with the computing device. In this example, the communication unit 240 may include a component for performing communication with an external device using a communication means such as Bluetooth, infrared, Zigbee, Wi-fi, and the like. The communication may include transmission and/or reception.

According to an embodiment, the communication unit 240 may be attached onto the mesh structure of the body unit. According to another embodiment, it may be configured in a structure formed separately from the mesh structure of the body unit. For example, it may be attached adjacent to the end of the mesh structure of the body unit in the longitudinal direction so as not to interfere with the stretchability of the remaining portion, or may be configured in a separately formed structure on one side of the circumference of the mesh structure.

Figure 3:
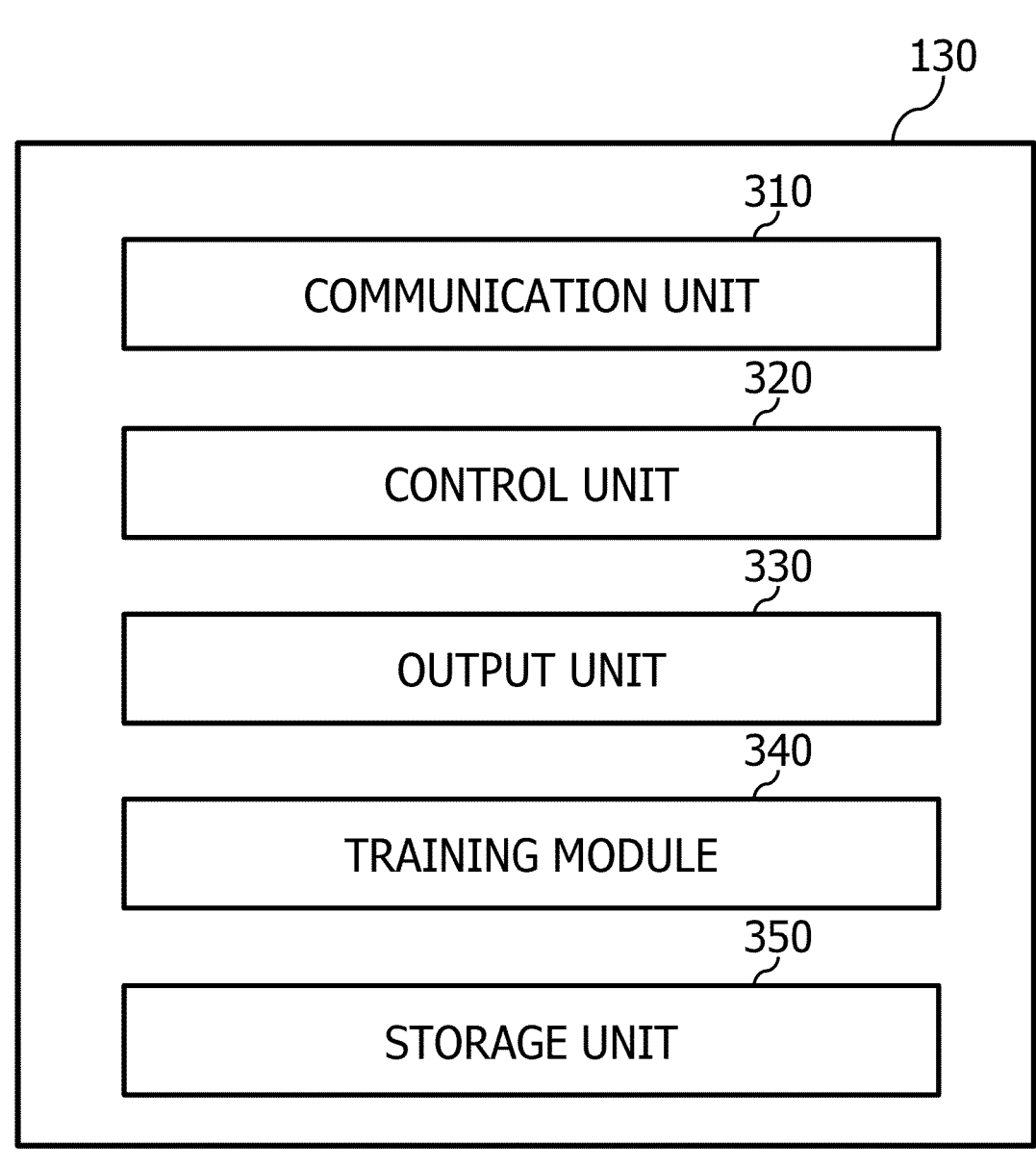
FIG. 3 is a block diagram illustrating in detail a configuration of a computing device according to an embodiment of the present disclosure.

FIG. 3 is a block diagram illustrating in detail the configuration of the computing device 130 according to an embodiment. The computing device 130 may be configured to include a communication unit 310, a control unit 320, an output unit 330, a training module 340, and a storage unit 350.

The communication unit 310 may be configured to communicate the data representing penis information with the device 110 for measuring penile erectile function. According to an embodiment, the communication unit 310 may be configured to communicate the first data representing position information on the penis with the device 110 for measuring penile erectile function. According to another embodiment, the communication unit 310 may be configured to communicate device identification information from each of a plurality of devices for measuring penile erectile function, and the first data representing position information on the penis measured by each of the plurality of devices for measuring penile erectile function. In this example, the communication may include transmission and/or reception.

The communication unit 310 may be configured to provide the data representing the penis information received from the device 110 for measuring penile erectile function to the control unit 320. According to an embodiment, the communication unit 310 may be configured to provide the first data representing position information on the penis received from the device 110 for measuring penile erectile function to the control unit 320.

The control unit 320 may be configured to generate the information on shape change of the penis based on the data representing penis information. The control unit 320 may be configured to provide the data representing penis information and/or the information on shape change of the penis to the output unit 330. The control unit 320 may be any one of a central processing unit (CPU), a graphic processing unit (GPU), and a digital signal processor (DSP), but is not limited thereto.

According to an embodiment, the information on shape change of the penis may be configured to include at least one of penis shape change information, information on comparison of the penis shape change information with pre-input data, and information on determination based on the penis shape change information. For example, the penis shape change information may be information that the circumference of the penis is "10 cm before erection, 13 cm after erection", and the information on comparison may be information that "the change of shape is greater than an average value", and the information on determination may be information that "the shape change of the penis or erectile function is within a normal range".

In the erectile function test system 100, the control unit 320 may be configured in the device for measuring penile erectile function, or configured in the computing device 130, or configured in both devices. According to an embodiment, when the device for measuring penile erectile function is configured to include a control unit, the communication unit 310 of the computing device 130 may be configured to communicate the information on shape change of the penis generated by the control unit of the device for measuring penile erectile function based on the data representing penis information through the communication unit of the device for measuring penile erectile function and the network 120.

According to another embodiment, when the device for measuring penile erectile function is configured to include a control unit, the communication unit 310 of the computing device 130 may be configured to receive the information on shape change of the penis generated by the control unit of the device for measuring penile erectile function based on the data representing penis information and provide the received information to the output unit 330. In this structure, since the device for measuring penile erectile function generates the information on shape change of the penis through the control unit, the computing device 130 may be configured such that it may not include the control unit.

The output unit 330 may be configured to output the information generated by the control unit 320 or the data representing penis information received through the communication unit 310 and/or the information generated based on the data. For example, the output unit 330 of the computing device 130 may be any device such as a display device or the like, for example, which is capable of outputting the information on shape change of the penis, and the information on shape change of the penis may be displayed on the display device and provided to a user (e.g., a clinician).

According to an embodiment, the erectile function test system 100 may include the body unit 210 having a mesh structure formed of stretchable material and configured to surround at least a portion of the penis, the sensor unit 220 arranged on the mesh structure of the body unit and configured to measure the first data representing position information on the penis, the storage unit 230 configured to store the first data, the communication unit 240 configured to communicate the first data with the computing device, the control unit 320 configured to generate the information on shape change of the penis based on the first data, and the output unit 330 configured to output the information on shape change of the penis.

The training module 340 may be configured to train an artificial neural network such that the information on shape change of the penis generated by the control unit 320 based on the first data received from each of the devices for measuring penile erectile function is input to an input layer of the artificial neural network and the information on whether or not the erectile function is normal is extracted. For example, the artificial neural network may employ one of a variety of artificial neural networks known in the field of artificial intelligence. When the shape change of the penis is generated based on the data received from the devices for measuring penile erectile function of a male, the control unit 320 may use the trained artificial neural network to extract the information on whether or not the erectile function of the male is normal, and the extracted information may be output to the output unit 330.

The storage unit 350 may be configured to store at least one of the data received through the communication unit 310 and the information on shape change of the penis generated from the control unit 320. According to an embodiment, the storage unit 350 may be configured to store at least one of the received first data and the information on shape change of the penis. The output unit 330 may be configured to output the data and/or information stored in the storage unit 350, and the communication unit 310 may be configured to communicate the data and/or information stored in the storage unit 350 with the device 110 for measuring penile erectile function and/or an external computing device.

According to an embodiment, the erectile function test system 100 may be configured to generate a blockchain, that is, a distributed ledger including blocks, and communicate with an external computing device. The control unit 320 may be configured to generate a distributed ledger formed of a plurality of blocks including a plurality of pieces of information on shape changes of penises. The plurality of blocks may be configured to include identification information of each of the plurality of devices for measuring penile erectile function, a block generation time, a hash reference to the distributed ledger, and the like.

According to an embodiment, the communication unit 310 may be configured to communicate the distributed ledger with an external computing device. The external computing device may be a plurality of nodes. The storage unit 350 may be configured to store the distributed ledger.

Blockchain technology uses a decentralized or distributed consensus mechanism. The computing device 130 records the history of information by using a distributed ledger shared with a plurality of nodes, and all validating nodes run the same (or agreed upon) consensus algorithm on the same information to approve (or disapprove) the information. With the use of the decentralized structure and consensus algorithm, forgery and alteration of transaction details by a third party is virtually impossible, and it is thus possible to ensure the reliability and transparency of information.

According to an embodiment, the control unit 320 may control the output unit 330 to output information on shape change of the penis according to a predetermined format. In this example, the format may be a type of information on shape change of the penis such as length or circumference, a method of representing information such as a chart or graph, a layout, that is, a screen composition, or a combination thereof. For example, the predetermined format may be configured to have, arranged therein, the information such as circumference, duration of erection, and the like of a penis necessary for analysis of the result of the survey provided by The International Index of Erectile Function (IIEF).

In an embodiment, the predetermined format may be pre-determined by the user. The storage unit 350 may be configured to store the predetermined format that is pre-determined by a user. The erectile function test system 100 is configured to output the information on shape change of the penis according to the predetermined format, so as to schematically output and show the information on shape change of the penis for the clinician, who is the user, to conveniently perform a clinical test.

Figure 4:
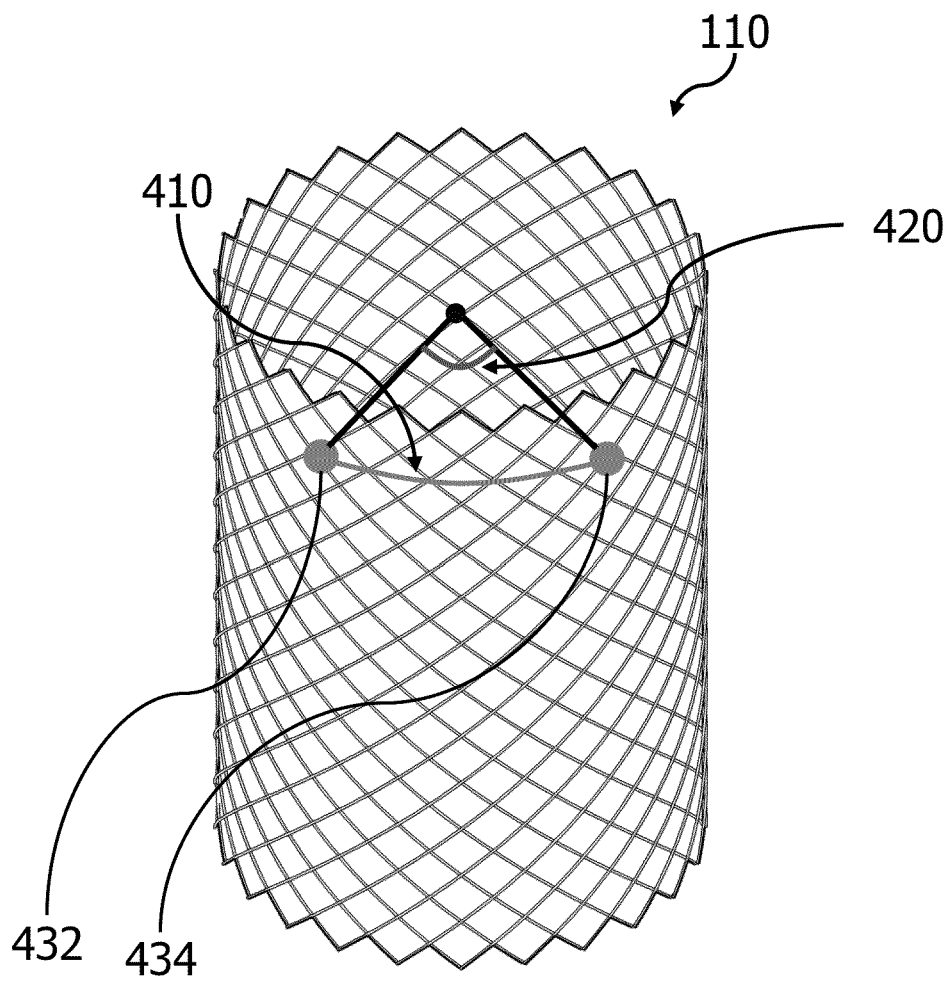
FIG. 4 is a perspective view illustrating a process of a control unit generating information on shape change of a penis from first data representing position information on the penis measured by a sensor unit according to an embodiment of the present disclosure.

FIG. 4 is a perspective view illustrating a process of the control unit 320 generating the information on shape change of the penis from the first data of the sensor according to an embodiment of the present disclosure. According to an embodiment, the control unit 320 may be configured to generate the information on shape change of the penis based on the first data representing position information on the penis. For example, the information on shape change of the penis may be configured to include at least one of information on length of the penis, information on degree of curvature of the penis, and information on circumference of the penis.

The information on shape change of the penis generated by the control unit 320 may include information on distance 410 between two position sensors on the penis and/or circumference of the penis. According to an embodiment, the control unit 320 may be configured to generate the information on distance 410 between the two position sensors on the penis based on the first data representing position information on the penis measured from two position sensors 432 and 434 forming the sensor unit 220 of the device 110 for measuring penile erectile function. Furthermore, the control unit 320 may generate the information on circumference of the penis by multiplying the distance 410 between the two position sensors by a reciprocal of a ratio of the distance 410 between the two position sensors to the entire circumference of the body unit known in advance, or by a reciprocal of a ratio of a separation angle 420 to 360°. In this example, the separation angle 420 may represent an angle formed between orthogonally projected line segments when a line segment extending from the center of the body unit 210 to each of the position sensors is orthogonally projected on a virtual plane including at least one position sensor and parallel to the circumferential direction of the body unit 210. In this process, the control unit 320 may be configured to assume that the cross-section of the penis has a circular shape or an elliptical shape with a specified ratio between long axis and short axis. In this process, the control unit 320 may be configured to assume that the mesh structure formed of stretchable material is uniformly stretched and contracted. For example, the sensor unit 220 may be configured such that the two position sensors are arranged with the separation angle 420 of 120° in the circumferential direction of the body unit, and the control unit 320 may be configured to assume that the cross-section of the penis has a circular shape. When the penis shape changes due to erection, the information on distance 410 between the two position sensors may be generated from the data of the two position sensors changed, and the information on distance 410 between the two position sensors may be multiplied by a reciprocal of the ratio of the distance of the two position sensors to the entire circumference of the body unit, that is, by 3, which is the reciprocal of 120°/360° so as to generate information on the entire penis circumference.

The information on shape change of the penis generated by the control unit 320 may include information on distance between two position sensors on the penis and/or length of the penis. According to an embodiment, the control unit 320 may be configured to generate distance information between two position sensors on the penis based on the first data representing position information on the penis measured from the two position sensors arranged in the longitudinal direction of the penis which form the sensor unit 220 of the device 110 for measuring penile erectile function, and generate the information on length of the penis by multiplying a reciprocal of a ratio of the distance between the two position sensors to a total length of the penis, which is known in advance.

The information on shape change of the penis generated by the control unit 320 may include information on a distance between the two position sensors on the penis and/or a degree of curvature of the penis. According to an embodiment, the sensors forming the sensor unit 220 may be configured such that two position sensors are arranged to be spaced apart in a longitudinal direction, and two other position sensors are arranged apart in parallel so that the sensor has a rectangular shape. Further, the control unit 320 may be configured to generate the distance information between two position sensors on the penis arranged to be spaced apart in the longitudinal direction based on the first data representing position information on the penis measured from the two sensors arranged to be spaced apart in the longitudinal direction, and generate the distance information based on the first data measured from two other position sensors. Furthermore, the control unit 320 may be configured to generate information that the penis is straight, that is, information that there is no degree of curvature when both distance information is the same as each other, and when one distance information is less than the other distance information, generate information on degree of curvature of the penis, including information that the penis is curved in a direction in which the distance information is small, or how much it is curved, according to the size of the difference between the distance information.

According to an embodiment, the information on shape change of the penis generated by the control unit may include 3D image information. The output unit 330 may be configured to output the information on shape change of the penis including a 3D image to the user. The 3D image information provides a visually excellent effect by allowing the user to see a variety of information such as length, circumference, degree of curvature, and the like at a glance.

According to an embodiment, the control unit 320 may be configured to generate 3D image information based on at least two pieces of 2D information. For example, the control unit 320 may be configured to generate 3D image information of the penis based on the information on circumference of the penis.

Figure 5:
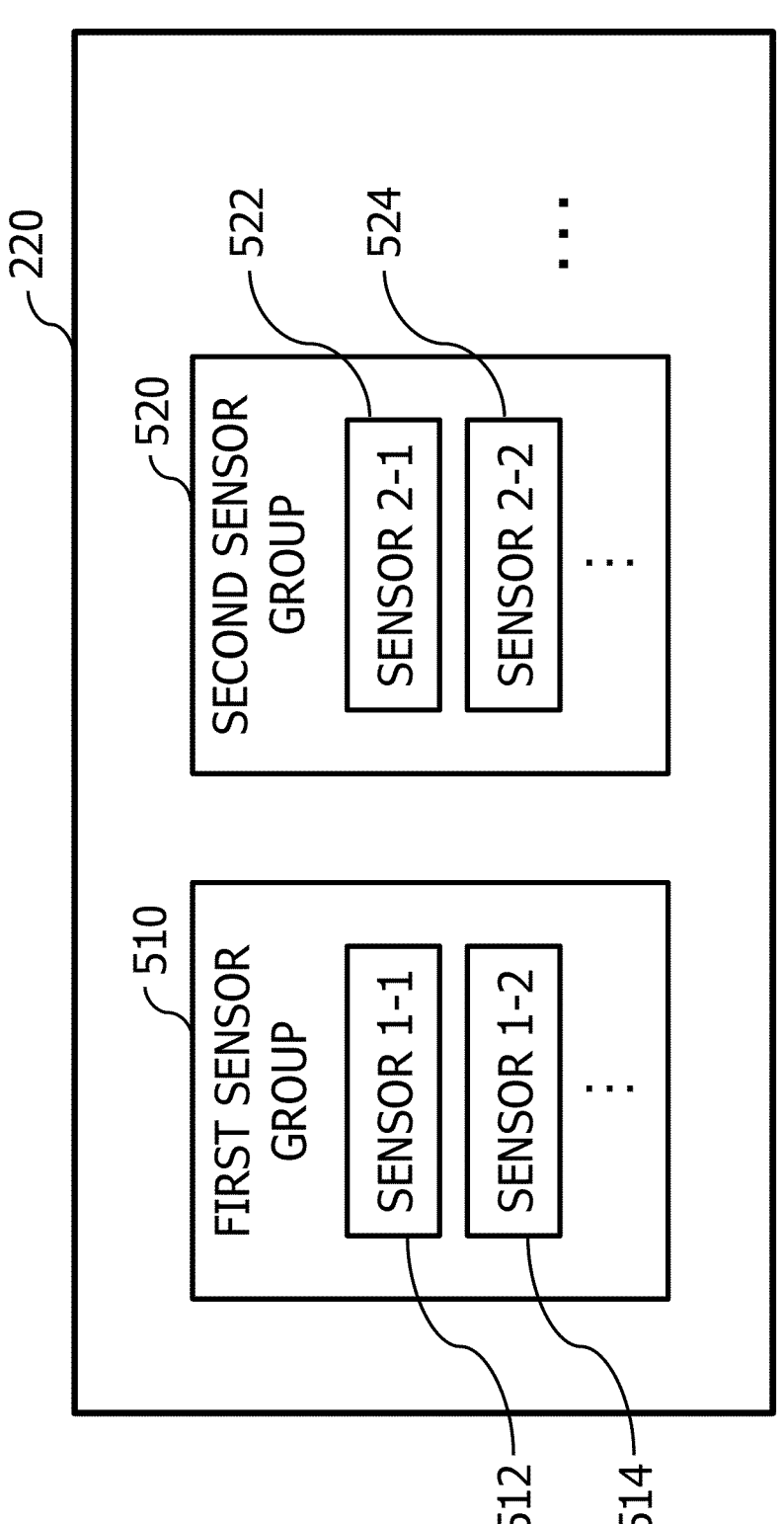
FIG. 5 is a block diagram illustrating in detail a configuration in which a sensor unit includes at least two sensor groups according to an embodiment of the present disclosure.

FIG. 5 is a block diagram illustrating in detail a configuration in which the sensor unit 220 includes at least two sensor groups 510 and 520 according to an embodiment of the present disclosure. According to an embodiment, the sensor unit 220 may include at least two sensor groups. For example, the sensor unit 220 may include two sensor groups, that is, a first sensor group 510 and a second sensor group 520, and each of the first sensor group and the second sensor group may include one or more sensors.

Figure 6:
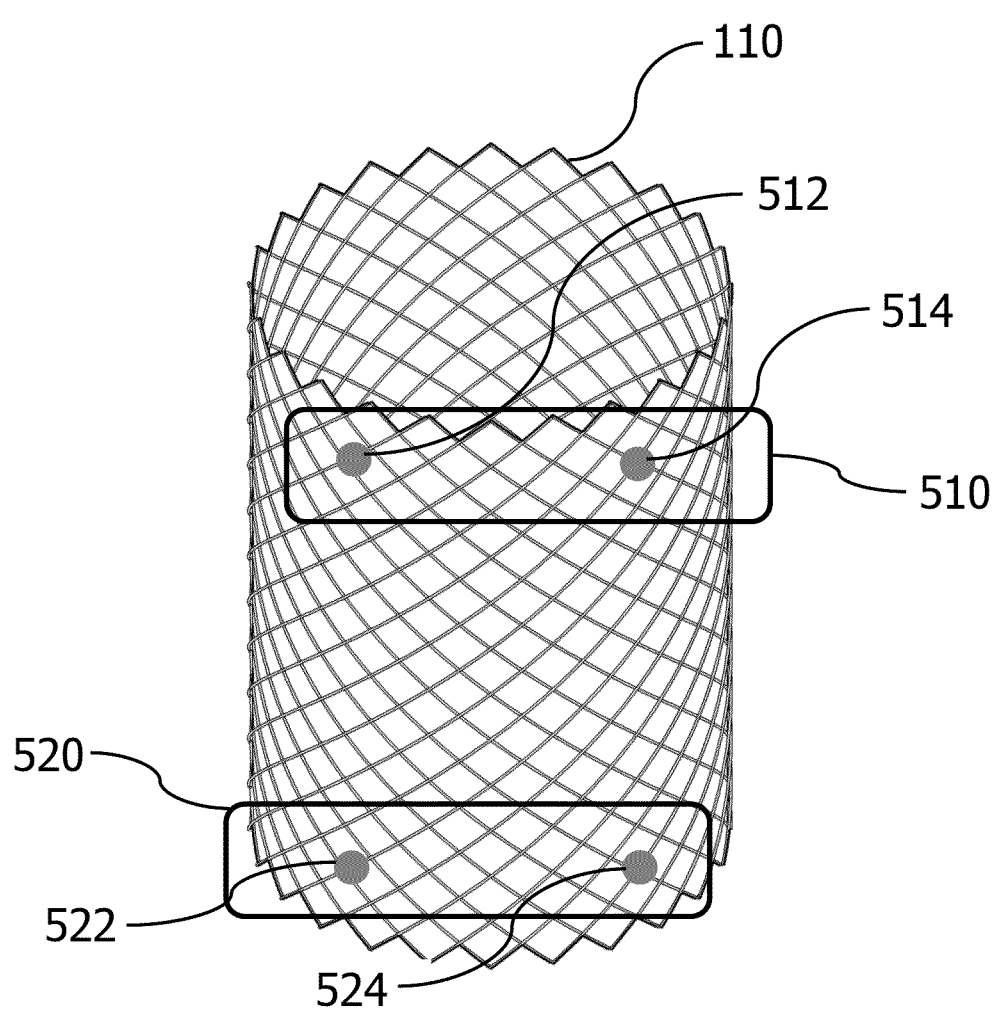
FIG. 6 is a perspective view illustrating the device for measuring penile erectile function in which the sensor unit is configured to include at least two sensor groups according to an embodiment of the present disclosure.

FIG. 6 is a perspective view illustrating the device 110 for measuring penile erectile function in which the sensor unit 220 is configured to include the at least two sensor groups 510 and 520 according to an embodiment of the present disclosure. According to an embodiment, the sensor unit 220 may be configured to include the at least two sensor groups 510 and 520, and may be configured such that the sensors of each sensor group, that is, sensors 512 and 514 of the first sensor group 510, and sensors 522 and 524 of the second sensor group 520 may be arranged to be spaced apart in the circumferential direction of the penis, respectively to measure the data representing penis information. For example, the sensors 512, 514, 522 and 524 may be configured to measure the first data representing position information on the penis.

Figure 7:
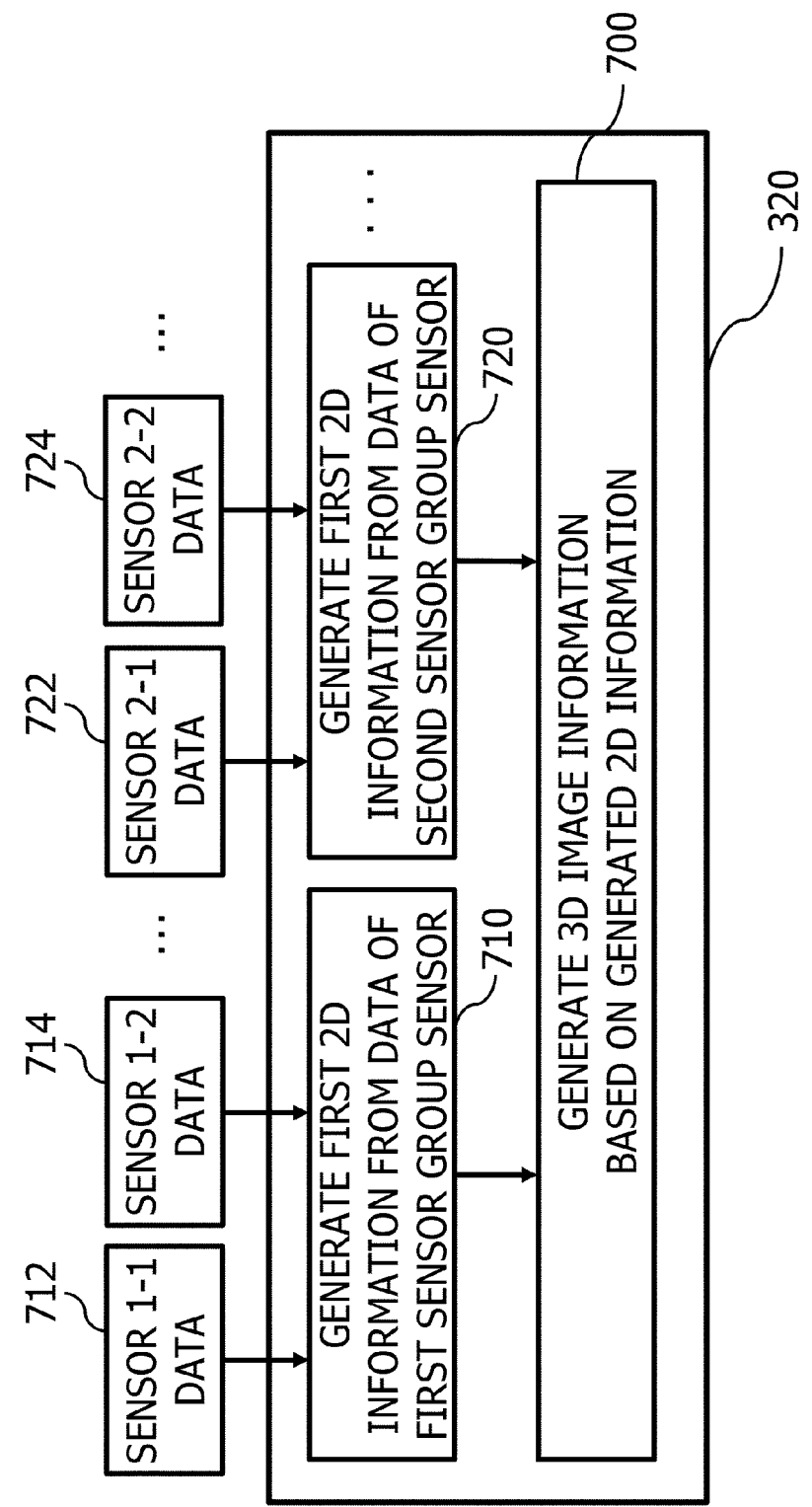
FIG. 7 is a flowchart illustrating a process of the control unit generating 3D image information based on first data representing position information on a penis measured by at least two sensor groups forming the sensor unit according to an embodiment of the present disclosure.

FIG. 7 is a flowchart illustrating a process of generating 3D image information based on the first data measured by the at least two sensor groups 510 and 520 forming the sensor unit 220 by the control unit 320 according to an embodiment of the present disclosure.

According to an embodiment, the control unit 320 may be configured to generate 2D information on shape change of the penis, respectively based on the data representing penis information measured from each of the first sensor group and the second sensor group, and generate 3D image information on shape change of the penis based on the 2D information. For example, the control unit 320 may be configured to generate the distance information between two position sensors based on the first data representing position information on the penis measured from the two position sensors 512 and 514 of the first sensor group 510 and generate the information on circumference of the penis based on this, and generate the distance information between two position sensors based on the first data representing position information on the penis measured from the two position sensors 522 and 524 of the second sensor group 520 and generate the information on circumference of the penis based on this. This is same as previously described in FIG. 4. Furthermore, the control unit 320 may be configured to generate 3D image information based on the generated information on circumference of the penis. In this process, the control unit 320 may be configured to assume that the penis has a truncated cone shape. The sensor unit 220 may be configured to have a large number of sensor groups, so that 3D image information further conforming to the actual shape of the penis may be generated. For example, by arranging the sensors for each node of the mesh structure of the body unit 210 and configuring the sensors arranged in the circumferential direction in one sensor group, 3D image information with high accuracy may be generated.

According to another embodiment, when there is a large number of sensors, the control unit 320 may generate 3D image information by introducing coordinates instead of the sensor groups. For example, the sensor unit 220 may be configured such that position sensors are arranged for each of the nodes of the mesh structure of the body unit 210, and each sensor may be configured to be assigned a coordinate such as (1,1) to (n,m). The control unit 320 may generate the information on shape change of the penis, including 3D image information, by arranging the first data representing position information on the penis measured by each sensor in accordance with the coordinates.

According to an embodiment, when the control unit 320 generates the information on shape change of the penis, the information on shape change of the penis may be configured to include information on stiffness of the penis. In the device 110 for measuring penile erectile function, the sensor unit 220 may be further configured to include a pressure sensor. According to an embodiment, the sensor unit 220 may be configured to measure second data representing pressure information of the penis, and the storage unit 230 may be configured to store second data, and the communication unit may be configured to communicate the second data to the computing device 130. According to an embodiment, the control unit 320 may be configured to generate the information on shape change of the penis based on the second data. Furthermore, when the control unit 320 generates the information on shape change of the penis, the information on shape change of the penis may be configured to include the information on stiffness based on the second data.

According to another embodiment, when the control unit 320 generates the information on shape change of the penis, the information on shape change of the penis may be configured to include the 3D image information and the information on stiffness of the penis. For example, the information on shape change of the penis may be configured to include information representing colors classified according to the three-dimensional penis shape and the stiffness of the penis. According to the present embodiment, the output unit 330 may display such that the user can effectively confirm the three-dimensional penis shape and the colors classified according to the stiffness of the penis at the same time.

Figure 8:
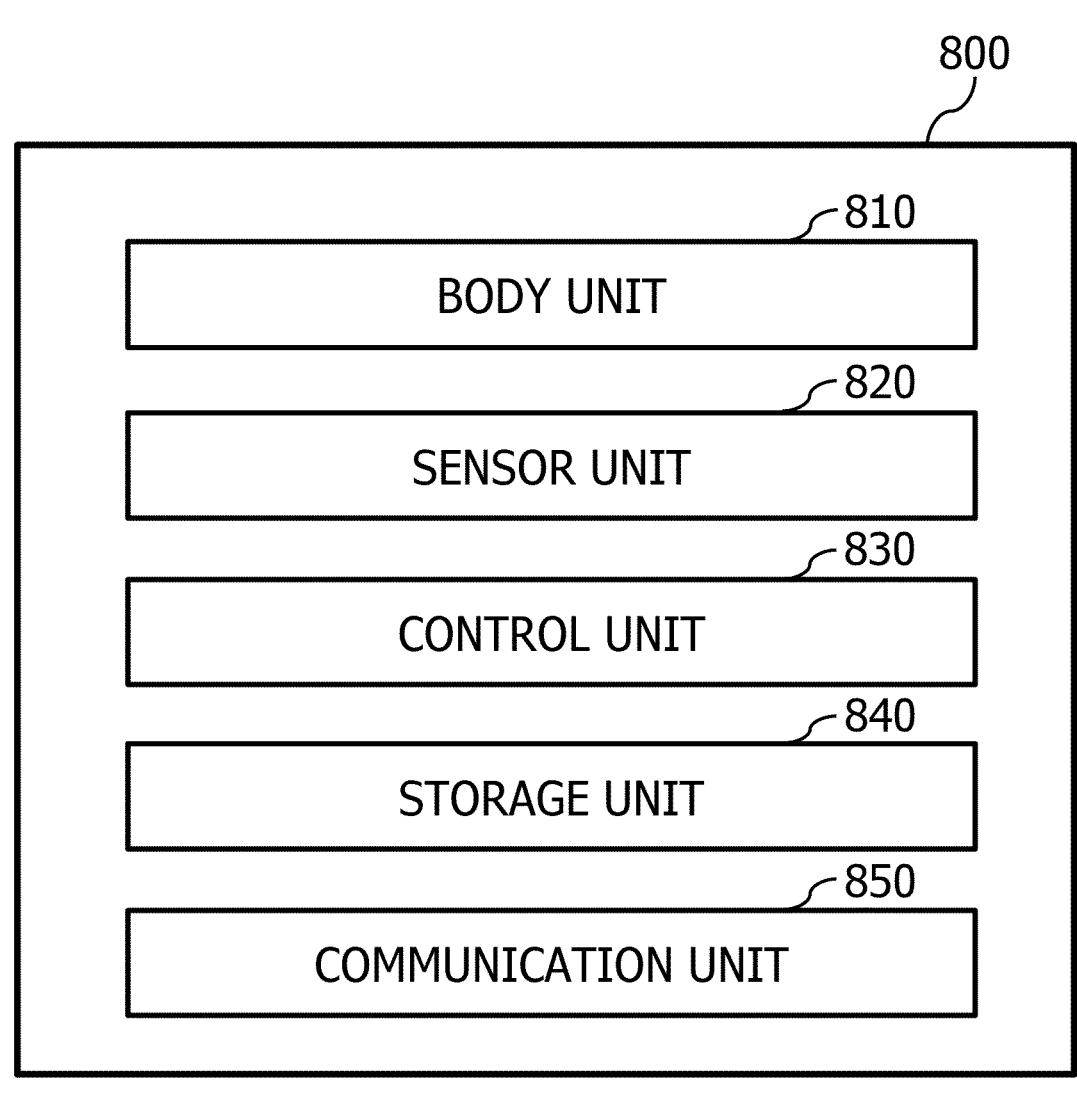
FIG. 8 is a block diagram illustrating in detail a configuration of a device for measuring penile erectile function further including a control unit according to an embodiment of the present disclosure.

FIG. 8 is a block diagram illustrating in detail the configuration of a device 800 for measuring penile erectile function further including a control unit 830 according to an embodiment of the present disclosure. In the erectile function test system 100, the control unit 830 may be configured in the device 800 for measuring penile erectile function, or configured in the computing device 130, or configured in both devices.

According to an embodiment, the device 800 for measuring penile erectile function may include a body unit 810 having a mesh structure formed of stretchable material and configured to surround at least a portion of the penis, a sensor unit 820 arranged on the mesh structure of the body unit and configured to measure the first data representing position information on the penis, the control unit 830 configured to generate the information on shape change of the penis based on the first data, a storage unit 840 configured to store at least one of the first data and the information on shape change of the penis generated by the control unit, and a communication unit 850 configured to communicate at least one of the first data and the information on shape change of the penis with the computing device 130.

According to an embodiment, the device 800 for measuring penile erectile function may include the body unit 810 having a mesh structure formed of stretchable material and configured to surround at least a portion of the penis, the sensor unit 820 arranged on the mesh structure of the body unit and configured to measure the first data representing position information on the penis, the control unit 830 configured to generate the information on shape change of the penis based on the first data, the storage unit 840 configured to store at least one of the first data and the information on shape change of the penis generated by the control unit, and the communication unit 850 configured to communicate at least one of the first data and the information on shape change of the penis with the computing device 130, in which the information on shape change of the penis may be configured to include at least one of information on length of the penis, information on degree of curvature of the penis, and information on circumference of the penis.

According to another embodiment, the device 800 for measuring penile erectile function may include the body unit 810 having a mesh structure formed of stretchable material and configured to surround at least a portion of the penis, the sensor unit 820 arranged on the mesh structure of the body unit and configured to measure the first data representing position information on the penis, the control unit 830 configured to generate the information on shape change of the penis based on the first data, the storage unit 840 configured to store at least one of the first data and the information on shape change of the penis generated by the control unit, and the communication unit 850 configured to communicate at least one of the first data and the information on shape change of the penis with the computing device 130, in which the sensor unit 820 may be configured to include at least two sensor groups, and the information on shape change of the penis may be configured to include 3D image information.

According to an embodiment, the device 800 for measuring penile erectile function may include the body unit 810 having a mesh structure formed of stretchable material and configured to surround at least a portion of the penis, the sensor unit 820 arranged on the mesh structure of the body unit and configured to measure the first data representing position information on the penis, the control unit 830 configured to generate the information on shape change of the penis based on the first data, the storage unit 840 configured to store at least one of the first data and the information on shape change of the penis generated by the control unit, and the communication unit 850 configured to communicate at least one of the first data and the information on shape change of the penis with the computing device 130, in which the sensor unit may be further configured to measure second data representing pressure information of the penis, the control unit 830 may be configured to generate the information on shape change of the penis based on at least one of the first data and the second data, the storage unit 840 may be further configured to store the second data measured by the sensor unit, and the communication unit 850 may be further configured to communicate the second data to the computing device.

According to an embodiment, the device 800 for measuring penile erectile function may include the body unit 810 having a mesh structure formed of stretchable material and configured to surround at least a portion of the penis, the sensor unit 820 arranged on the mesh structure of the body unit and configured to measure the first data representing position information on the penis, the control unit 830 configured to generate the information on shape change of the penis based on the first data, the storage unit 840 configured to store at least one of the first data and the information on shape change of the penis generated by the control unit, and the communication unit 850 configured to communicate at least one of the first data and the information on shape change of the penis with the computing device 130, in which the sensor unit may be further configured to measure second data representing pressure information of the penis, the control unit 830 may be configured to generate the information on shape change of the penis based on at least one of the first data and the second data, the storage unit 840 may be further configured to store the second data measured by the sensor unit, and the communication unit 850 may be further configured to communicate the second data to the computing device, and the information on shape change of the penis may be further configured to include information on stiffness of the penis based on the second data.

According to an embodiment, when the device 800 for measuring penile erectile function is configured to include the control unit 830, the communication unit 310 of the computing device 130 may be configured to communicate the information on shape change of the penis generated by the control unit 830 of the device 800 for measuring penile erectile function based on the data representing penis information through the communication unit 850 of the device 800 for measuring penile erectile function and the network 120. Further, when the device 800 for measuring penile erectile function is configured to include the control unit 830, the communication unit 310 of the computing device 130 may be configured to receive the information on shape change of the penis generated by the control unit 830 of the device 800 for measuring penile erectile function based on the data representing penis information and provide the received information to the output unit 330. For example, the communication unit 310 of the computing device 130 may be configured to receive the information on shape change of the penis including 3D image information from the communication unit 850 of the device 800 for measuring penile erectile function and provide the received information to the output unit 330.

Figure 9:
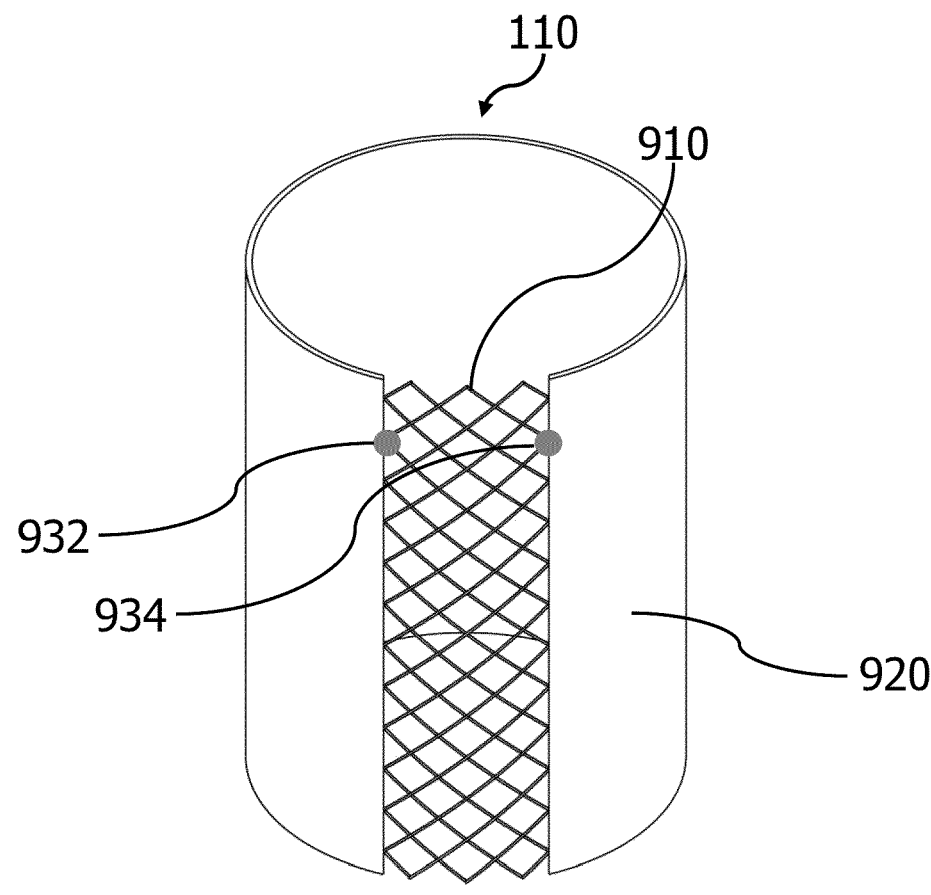
FIG. 9 is a perspective view illustrating a configuration of a device for measuring penile erectile function, in which a portion of a body unit has a mesh structure formed of stretchable material, and the remaining portion of the body unit is formed of non-stretchable material according to an embodiment of the present disclosure.

FIG. 9 is a perspective view illustrating a configuration of the device 110 for measuring penile erectile function, in which a portion of the body unit 210 has a mesh structure 910 formed of stretchable material, and the remaining portion of the body unit is formed of non-stretchable material according to an embodiment of the present disclosure.

The mesh structure 910 formed of stretchable material can be curved, and the material itself can be stretched and contracted. For example, the mesh structure 910 formed of stretchable material may be formed of a material including rubber. The portion 920 formed of non-stretchable material can be curved, but the material itself cannot be stretched. For example, the portion 920 formed of non-stretchable material may be formed of a material including a plastic film.

According to an embodiment, the device 110 for measuring penile erectile function may include the body unit 900 having a mesh structure formed of stretchable material and configured to surround at least a portion of the penis, the sensor unit 220 arranged on the mesh structure of the body unit and configured to measure the first data representing position information on the penis, the storage unit 230 configured to store the first data, and the communication unit 240 configured to communicate the first data with the computing device 130. A portion of the body unit 900 may be formed of a mesh structure 910 formed of stretchable material, and the remaining portion of the body unit 900 may be formed of non-stretchable material.

Figure 10:
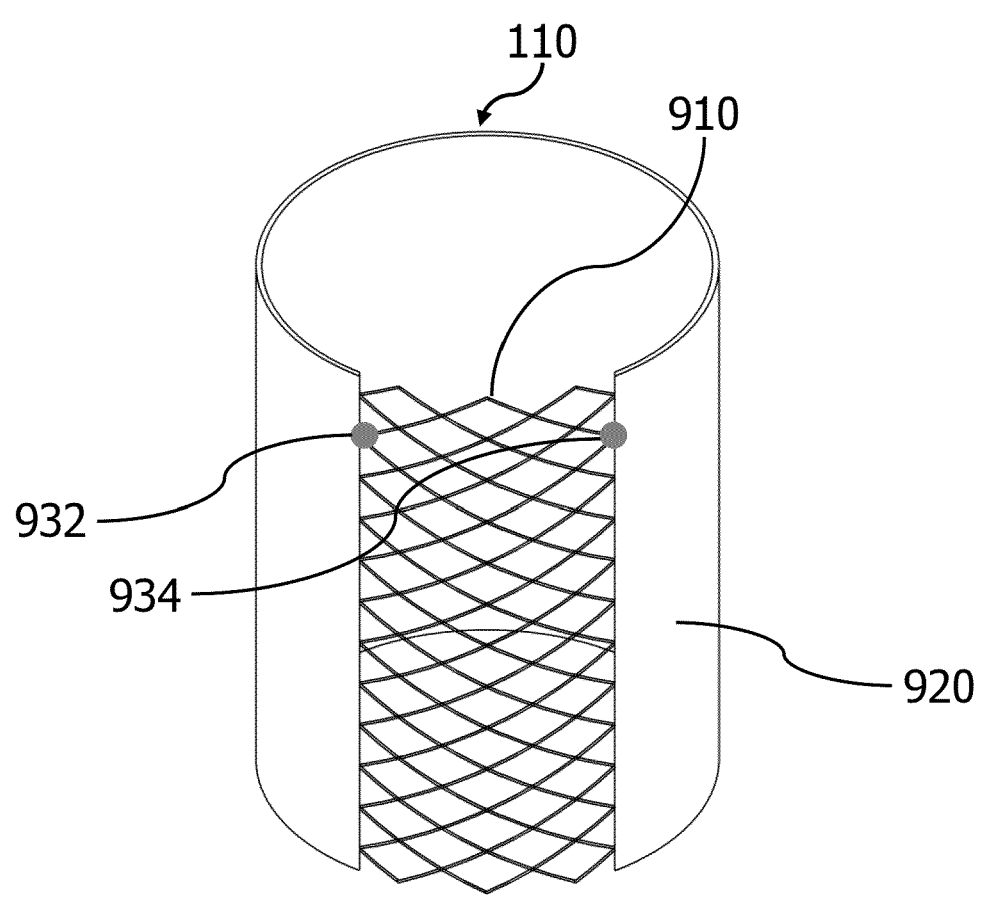
FIG. 10 is a perspective view illustrating that the device for measuring penile erectile function is deformed according to a shape change of a penis, in which a portion of the body unit according to an embodiment of the present disclosure has a mesh structure formed of stretchable material, and the remaining portion of the body unit is formed of non-stretchable material.

FIG. 10 is a perspective view illustrating that the device for measuring penile erectile function is deformed according to a shape change of the penis, in which a portion of the body unit 210 of the device 110 for measuring penile erectile function according to an embodiment of the present disclosure has the mesh structure 910 formed of stretchable material, and the remaining portion of the body unit is formed of non-stretchable material.

When the shape of the penis changes due to erection, the circumference of the device for measuring penile erectile function also changes, in which the portion 920 formed of non-stretchable material may be curved and deformed in shape, but with the material itself that cannot be stretched, the circumference remains unchanged, while the mesh structure 910 formed of stretchable material is stretched to be changed in the circumference. In this case, the amount of change in the circumference of the penis is the same as the amount of change in the circumference of the mesh structure 910 formed of stretchable material. According to an embodiment, the control unit may calculate a distance between two position sensors based on the first data representing position information on the penis obtained from the two position sensors with respect to the shape change of the penis before and after erection, and generate the information on circumference of the penis by adding the circumference length of the portion 920 formed of non-stretchable material, which is known in advance. For example, the circumference of the portion 920 formed of non-stretchable material may be 5 cm, and the position sensors may be arranged at both ends of the circumference of the mesh structure 910 formed of stretchable material. When the shape of the penis changes due to erection, information on the entire circumference of the penis may be generated by generating distance information of two position sensors from the changed first data and by adding 5 cm.

According to this embodiment, there is no need for a process of multiplying by the reciprocal of the ratio of the distance between the two position sensors to the entire circumference of the body unit or by the reciprocal of the ratio of the separation angle 420 to 360°. In addition, there is no need for a process of assuming the cross-section to be in circular shape, or an elliptical shape with a specified ratio of the long axis and the short axis, or assuming that the mesh structure formed of stretchable material is stretched uniformly. As a result, there is an excellent effect of reducing errors in the information on the actual shape of the penis and improving accuracy of erectile function measurement and test results.

Figure 11:
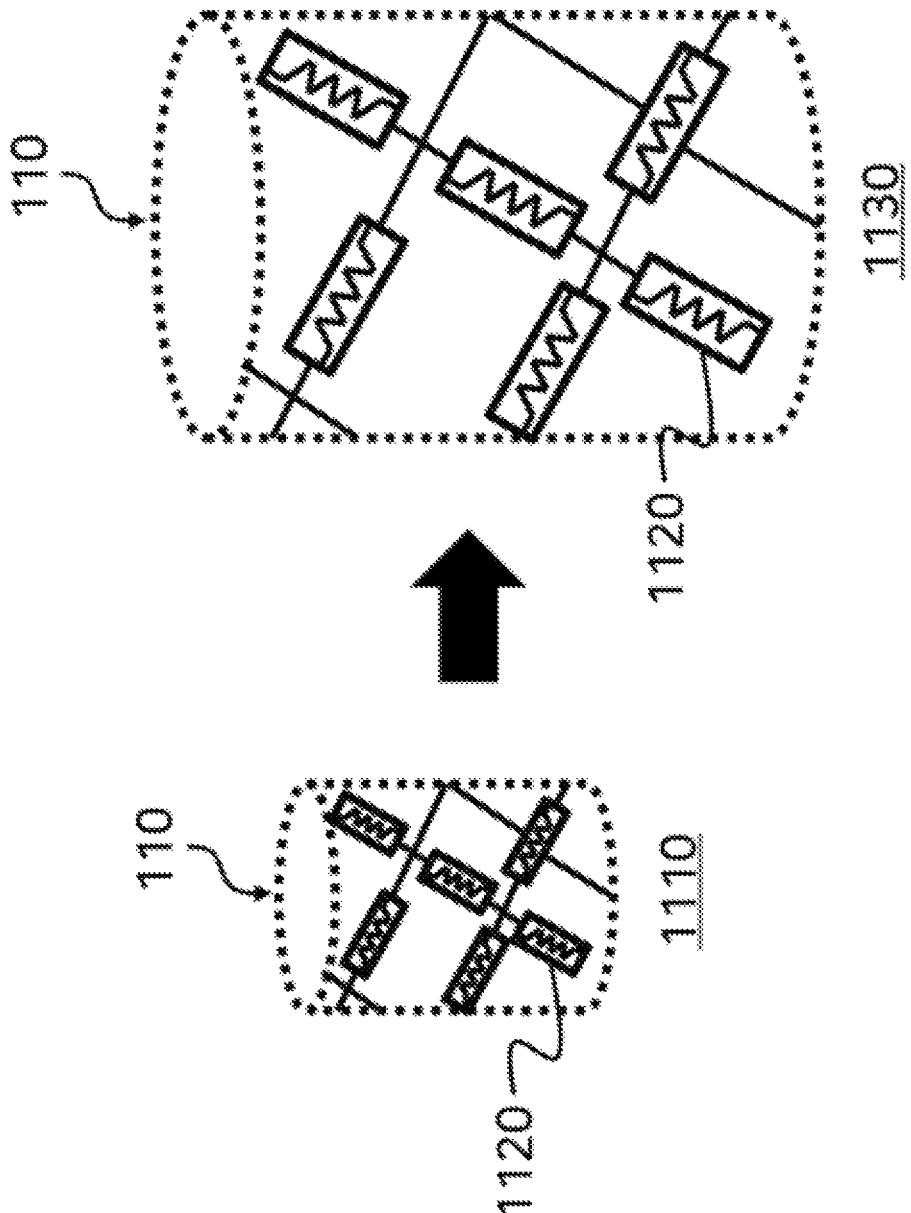
FIG. 11 is an exemplary diagram illustrating a device for measuring penile erectile function in which a body unit and a sensor unit are formed of stretchable material, and connected to a computing device by wire.

FIG. 11 is an exemplary diagram illustrating the device 110 for measuring penile erectile function in which the body unit and the sensor unit are formed of stretchable material, and connected to the computing device 130 by wire. In this example, the body unit may be formed of stretchable material and have any shape that is capable of enclosing the penis of the male. For example, the body unit may have a shape that is formed of a mesh structure, but is not limited thereto. According to an embodiment, the device 110 for measuring penile erectile function may be configured such that one or more stretchable sensors 1120 are attached to the body unit thereof. In this example, the stretchable sensor 1120 may be stretched according to whether the body unit is stretched or not, and may refer to any sensor that includes a resistance element, and may include an e-textile, stretch sensor, and the like, for example, but is not limited thereto.

In FIG. 11, a state 1110 of the device 110 for measuring penile erectile function may represent the device 110 for measuring penile erectile function worn on the penis of the male user in the state before erection. In this case, when a current flows through the stretchable sensor 1120 of the device 110 for measuring penile erectile function, a specific resistance value may be measured. According to an embodiment, the device 110 for measuring penile erectile function may include a communication unit (not shown) configured to communicate with a computing device (not shown) by wire, and the computing device may control so that the current flows through the stretchable sensor 1120 of the device 110 for measuring penile erectile function, and may receive a resistance value measured with the stretchable sensor 1120, or calculate the resistance value based on a signal received from the stretchable sensor 1120. As shown, the computing device may determine information on at least one of size, thickness, and degree of curvature of the penis of a male user wearing the device 110 for measuring penile erectile function based on the resistance values measured from a plurality of stretchable sensors 1120.

In FIG. 11, a state 1130 of the device 110 for measuring penile erectile function may represent the device 110 for measuring penile erectile function worn on the penis of the male user in the state after erection. In the state of erection, the computing device may allow current to flow through the stretchable sensor 1120, and may receive a resistance value measured with the stretchable sensor 1120, or calculate a resistance value based on a signal received from the stretchable sensor 1120. In this case, the computing device may determine information changed in at least one of the size, the thickness, and the degree of curvature of the penis of the male user wearing the device 110 for measuring penile erectile function, that is, may determine the information on shape change of the penis based on the change in the resistance value measured from the stretchable sensor 1120 of the device 110 for measuring penile erectile function.

For example, as illustrated, when the stretchable sensor 1120 including the resistance element is stretched, the resistance value measured after the erection may increase to be greater than the resistance value measured before the erection. Accordingly, the computing device may measure the change in the size and/or the thickness of the penis of the male wearing the device 110 for measuring penile erectile function through the degree of increase in the resistance value. According to still another embodiment, the computing device may be configured to measure not only the degree of stretching of the stretchable sensor 1120, but also the direction in which it is stretched, and/or information about its position, and the computing device may be configured to measure the degree of curvature of the penis of the male user based on the measured information.

Figure 12:
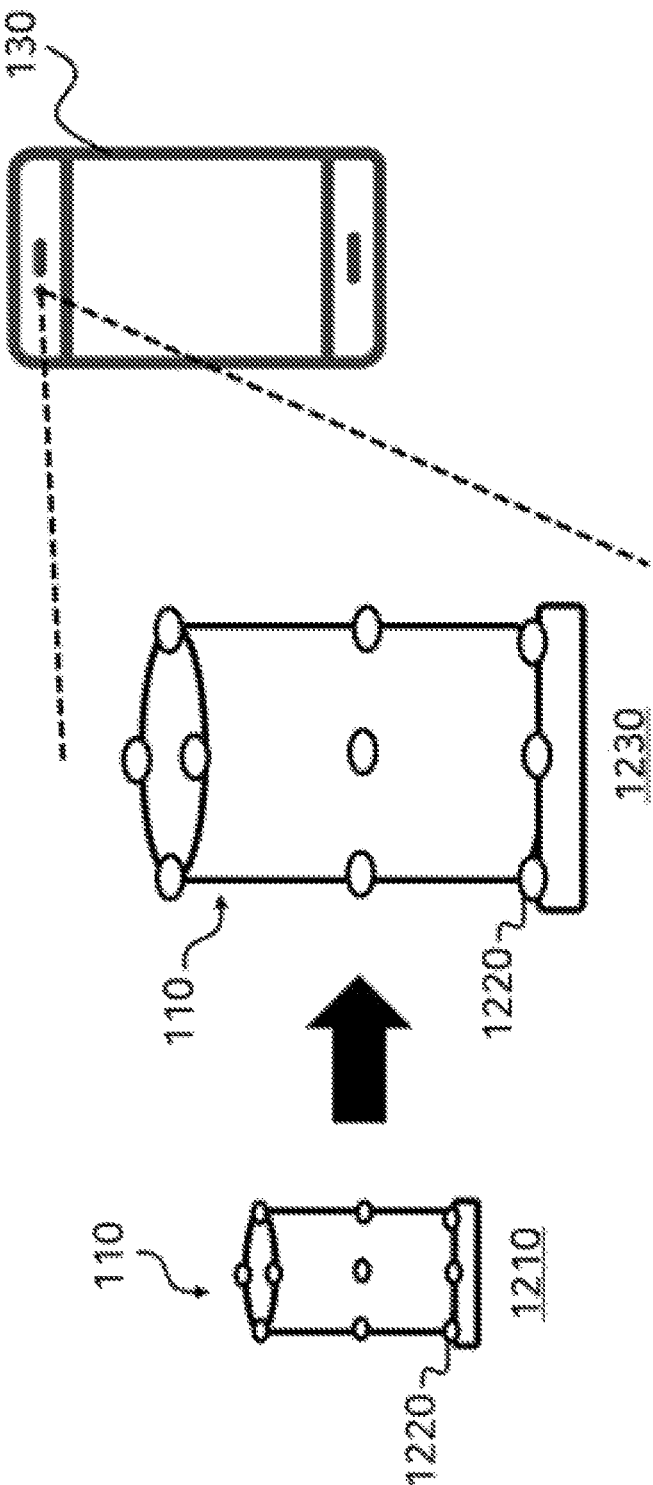
FIG. 12 is an exemplary diagram illustrating a device 110 for measuring penile erectile function in which an optical marker is attached to a body unit and capable of imaging by an image sensor of the computing device 130 according to an embodiment of the present disclosure.

FIG. 12 is an exemplary diagram illustrating the device 110 for measuring penile erectile function in which an optical marker 1220 is attached to the body unit and capable of imaging by an image sensor of the computing device 130 according to an embodiment of the present disclosure. According to an embodiment, the device 110 for measuring penile erectile function may be configured such that one or more optical markers 1220 are attached to the body unit. In this example, the optical marker 1220 may refer to any sensor that can measure the position of the attached optical marker 1220 upon imaging by an image sensor (e.g., a camera) of the computing device 130, and may include a reflector, an LED device, and the like, for example, but is not limited thereto. In this example, the body unit may be formed of stretchable material and have any shape that is capable of enclosing the penis of the male. For example, the body unit may have a shape that is formed of a mesh structure, but is not limited thereto.

In FIG. 12, a state 1210 of the device 110 for measuring penile erectile function may represent the device 110 for measuring penile erectile function worn on the penis of the male user in the state before erection. In this case, when the device 110 for measuring penile erectile function is captured or photographed by the image sensor of the computing device 130, the positions of a plurality of optical markers 1220 can be determined from the image of the captured or photographed device 110 for measuring penile erectile function. The computing device may determine information on at least one of the size, the thickness, and the degree of curvature of the penis of the male user wearing the device 110 for measuring penile erectile function based on the positions of the plurality of optical markers 1220.

In FIG. 12, a state 1230 of the device 110 for measuring penile erectile function may represent the device 110 for measuring penile erectile function worn on the penis of the male user in the state after erection. In the state of erection, when the device 110 for measuring penile erectile function is captured by the image sensor of the computing device 130, the positions of the optical markers 1220 of the device 110 for measuring penile erectile function may be measured. In this case, the computing device 130 may determine information changed in at least one of the size, the thickness, and the degree of curvature of the penis of the male user wearing the device 110 for measuring penile erectile function, that is, the information on shape change of the penis based on the change in positions of the plurality of optical markers 1220 of the device 110 for measuring penile erectile function.

According to an embodiment, healthcare facility staff (e.g., doctor, nurse, person in charge of examination, and the like) may directly hold the computing device 130 and capture an image of the device 110 for measuring penile erectile function. According to another embodiment, the computing device 130 may be positioned at any position in which the device 110 for measuring penile erectile function can be measured. For example, the computing device 130 may be positioned on the top, bottom, and/or side of a user wearing the device 110 for measuring penile erectile function. In addition, for situations in which the user wearing the device 110 for measuring penile erectile function moves (e.g., when he turns over), the computing device 130 may be mounted on any device that is configured to sense the device 110 for measuring penile erectile function and/or the optical markers 1220 and move the computing device 130 so that the computing device 130 can capture an image of the device 110 for measuring penile erectile function.

In a hardware implementation, the computing device and/or the device for measuring penile erectile function may include processors or processing units for use in performing the techniques. The processors or processing units may be implemented in one or more ASICs, DSPs, digital signal processing devices (DSPDs), programmable logic devices (PLDs), field programmable gate arrays (FPGAs), processors, controllers, microcontrollers, microprocessors, electronic devices, other electronic units designed to perform the functions described in the present disclosure, computers, or a combination thereof.

Accordingly, various example processors and logic blocks, modules, and circuits described in connection with the present disclosure may be implemented or performed with general purpose processors, DSPs, ASICs, FPGAs or other programmable logic devices, discrete gate or transistor logic, discrete hardware components, or any combination of those designed to perform the functions described herein. The general purpose processor may be a microprocessor, but in the alternative, the processor may be any related processor, controller, microcontroller, or state machine. The processor may also be implemented as a combination of computing devices, for example, a DSP and microprocessor, a plurality of microprocessors, one or more microprocessors associated with a DSP core, or any other combination of the configurations.

In the implementation using firmware and/or software, the techniques may be implemented with instructions stored on a computer-readable medium, such as random access memory (RAM), read-only memory (ROM), non-volatile random access memory (NVRAM), programmable read-only memory (PROM), erasable programmable read-only memory (EPROM), electrically erasable PROM (EE-PROM), flash memory, compact disc (CD), magnetic or optical data storage devices, and the like. The instructions may be executable by one or more processors, and may cause the processor(s) to perform certain aspects of the functions described in the present disclosure.

When implemented in software, the techniques may be stored on a computer-readable medium as one or more instructions or codes, or may be transmitted through a computer-readable medium. The computer-readable media include both the computer storage media and the communication media including any medium that facilitates the transfer of a computer program from one place to another. The storage media may also be any available media that may be accessed by a computer. By way of non-limiting example, such a computer-readable medium may include RAM, ROM, EEPROM, CD-ROM or other optical disk storage, magnetic disk storage or other magnetic storage devices, or any other media that can be used to transfer or store desired program code in the form of instructions or data structures and can be accessed by a computer. Also, any connection is properly referred to as a computer-readable medium.

For example, when the software is transmitted from a website, server, or other remote sources using coaxial cable, fiber optic cable, twisted pair, digital subscriber line (DSL), or wireless technologies such as infrared, wireless, and microwave, the coaxial cable, the fiber optic cable, the twisted pair, the digital subscriber line, or the wireless technologies such as infrared, wireless, and microwave are included within the definition of the medium.

The software module may reside in, RAM memory, flash memory, ROM memory, EPROM memory, EEPROM memory, registers, hard disk, removable disk, CD-ROM, or any other form of storage medium known. An exemplary storage medium may be connected to the processor, such that the processor may read or write information from or to the storage medium. Alternatively, the storage medium may be integrated into the processor. The processor and the storage medium may exist in the ASIC. The ASIC may exist in the user terminal. Alternatively, the processor and storage medium may exist as separate components in the user terminal.

Although the embodiments described above have been described as utilizing aspects of the currently disclosed subject matter in one or more standalone computer systems, the present disclosure is not limited thereto, and may be implemented in conjunction with any computing environment, such as a network or distributed computing environment. Furthermore, aspects of the subject matter in the present disclosure may be implemented in multiple processing chips or devices, and storage may be similarly influenced across a plurality of devices. Such devices may include PCs, network servers, and portable devices.

Although the present disclosure has been described in connection with some embodiments herein, various modifications and changes can be made without departing from the scope of the present disclosure, which can be understood by those skilled in the art to which the present disclosure pertains. Further, such modifications and changes are intended to fall within the scope of the claims appended herein.

What is claimed is:

1. A device for measuring penile erectile function, comprising:
   a cylindrical body unit having a mesh structure formed of stretchable material and a non-mesh portion formed of non-stretchable material and configured to surround at least a portion of a penis, wherein the non-mesh portion includes a first edge extending in a height direction of the cylindrical body unit and a second edge extending in the height direction and constitutes a lateral surface of the cylindrical body unit with a gap between the first edge and the second edge, the mesh structure is attached between the first edge and the second edge to fill the gap, the non-mesh portion covers more than half of a circumference of the cylindrical body unit, and the non-mesh portion is formed of a plastic film and deformed in shape in response to an erection of the penis;
   a sensor unit arranged on the mesh structure of the cylindrical body unit and configured to measure first data representing position information on the penis, wherein the sensor unit includes a first position sensor arranged at one end of the mesh structure and a second position sensor arranged at the other end of the mesh structure, the first position sensor is configured to measure a first relative position of the first position sensor on the penis and the second position sensor is configured to measure a second relative position of the second position sensor;

a control unit configured to calculate a distance between the first position sensor and the second position sensor based on the first relative position of the first position sensor and the second relative position of the second position sensor and generate information on shape change of the penis based on the first data;
   a storage unit configured to store at least one of the first data and the information on shape change of the penis and a predetermined circumference length of the non-mesh portion extending from the first edge to the second edge; and
   a communication unit configured to communicate at least one of the first data and the information on shape change of the penis with a computing device,
   wherein the control unit is further configured to generate information on a circumference length of the penis by adding the predetermined circumference length of the non-mesh portion and the distance between the first position sensor and the second position sensor.

2. The device for measuring penile erectile function according to claim 1, wherein the information on shape change of the penis is further configured to include at least one of information on length of the penis, information on degree of curvature of the penis, and information on the circumference of the penis.

3. The device for measuring penile erectile function according to claim 1, wherein the information on shape change of the penis is further configured to include 3D image information.

4. The device for measuring penile erectile function according to claim 1, wherein
   the sensor unit is further configured to measure second data representing pressure information of the penis,
   the control unit is further configured to generate the information on shape change of the penis based on at least one of the first data and the second data,
   the storage unit is further configured to store the second data measured by the sensor unit, and
   the communication unit is further configured to communicate the second data to the computing device.

5. The device for measuring penile erectile function according to claim 4, wherein the information on shape change of the penis is further configured to include information on stiffness of the penis based on the second data.

6. A device for measuring penile erectile function, comprising:
   a cylindrical body unit having a mesh structure formed of stretchable material;
   a sensor unit arranged on the mesh structure of the cylindrical body unit and configured to measure first data representing position information on a penis, wherein the sensor unit includes a first position sensor, a second position sensor, a third position sensor, and a fourth position sensor, the first position sensor and the second position sensor are arranged apart in a circumferential direction of the cylindrical body and the third position sensor and the fourth position sensor are arranged part in the circumferential direction of the cylindrical body such that the first position sensor, the second position sensor, the third position sensor, and the fourth position sensor are arranged in a rectangular shape, the first position sensor is configured to measure a first relative position of the first position sensor on the penis, the second position sensor is configured to measure a second relative position of the second position sensor, the third position sensor is configured to measure a third relative position of the third position sensor on the penis, the fourth position sensor is configured to measure a fourth relative position of the fourth position sensor;

a control unit configured to:

calculate a first distance between the first position sensor and the third position sensor in a longitudinal direction of the cylindrical body unit based on the first relative position of the first position sensor and the third relative position of the third position sensor;

calculate a second distance between the second position sensor and the fourth position sensor in a longitudinal direction of the cylindrical body unit based on the second relative position of the second position sensor and the fourth relative position of the fourth position sensor;

determine whether the first distance is different from the second distance; and determine a degree of curvature of the penis and a curved direction of the penis based on a difference between the first distance and the second distance;

a storage unit configured to store at least one of the first data and information on shape change of the penis including the degree of curvature of the penis and the curved direction of the penis; and a communication unit configured to communicate at least one of the first data and the information on shape change of the penis with a computing device.

* * * * *